(12) United States Patent
Wang Chi

(10) Patent No.: US 9,285,666 B2
(45) Date of Patent: Mar. 15, 2016

(54) OBJECT GUIDE SYSTEM

(71) Applicant: EUE MEDICAL TECHNOLOGY CO., LTD., Taipei (TW)

(72) Inventor: Hsiu-Mien Wang Chi, Taipei (TW)

(73) Assignee: EUE MEDICAL TECHNOLOGY CO., LTD., Taipei (TW)

( * ) Notice: Subject to any disclaimer, the term of this patent is extended or adjusted under 35 U.S.C. 154(b) by 90 days.

(21) Appl. No.: 14/253,940

(22) Filed: Apr. 16, 2014

(65) Prior Publication Data
US 2015/0301439 A1    Oct. 22, 2015

(51) Int. Cl.
| | |
|---|---|
| *G03B 21/14* | (2006.01) |
| *G03B 21/20* | (2006.01) |
| *A61B 17/00* | (2006.01) |
| *A61B 19/00* | (2006.01) |
| *G06F 19/00* | (2011.01) |

(52) U.S. Cl.
CPC ............ *G03B 21/2053* (2013.01); *A61B 17/00* (2013.01); *A61B 19/20* (2013.01); *A61B 19/5244* (2013.01); *G06F 19/321* (2013.01); *G06F 19/3406* (2013.01); *G06F 19/3481* (2013.01)

(58) Field of Classification Search
CPC ........ G03B 15/14; A61B 17/00; A61B 19/20; A61B 19/5244; A61B 2019/5293; A61B 2019/5295; G06F 19/321; G06F 19/3406; G06F 19/3481
See application file for complete search history.

(56) References Cited

U.S. PATENT DOCUMENTS

| | | | | |
|---|---|---|---|---|
| 5,715,836 A * | 2/1998 | Kliegis | ................ | G06F 19/3481 600/425 |
| 5,792,147 A * | 8/1998 | Evans | .................... | A61B 19/20 606/130 |
| 2014/0177909 A1* | 6/2014 | Lin | .................... | G06K 9/00355 382/103 |
| 2015/0051725 A1* | 2/2015 | Lee | ........................ | G09B 23/28 700/98 |
| 2015/0182293 A1* | 7/2015 | Yang | ..................... | A61B 5/064 600/424 |

* cited by examiner

*Primary Examiner* — William C Dowling
*Assistant Examiner* — Magda Cruz
(74) *Attorney, Agent, or Firm* — CKC & Partners Co., Ltd.

(57) ABSTRACT

An object guide system includes a plurality of light projecting devices, at least one image capture device, a control device electrically coupled with the light projecting devices, and a display unit electrically coupled with the at least one image capture device and the control device. When an object enters an operation space, a projected information is imaged on the object. Then, the at least one image capture device captures the cross information of the operation space and the three-dimensional position information of the object. Then, the control device calculates the coordinates of the object that is moving in the operation space. Thus, after the at least one image capture device captures the cross information of the operation space and the three-dimensional position information of the object, the object guide system proceeds interactive and guiding operations.

3 Claims, 5 Drawing Sheets

OBJECT GUIDE SYSTEM

BACKGROUND OF THE INVENTION

1. Field of the Invention

The present invention relates to a guide system and, more particularly, to an object guide system available for medical, amusement or other uses.

2. Description of the Related Art

A surgeon has to prepare two-dimensional cross-sectional images of a computed tomography (CT) or nuclear magnetic resonance (NMR) of a patient before surgery. After inspecting the two-dimensional images, the surgeon rebuilds three-dimensional images and imagines the location of the patient's lesion, so as to program the surgical contents, including entry points, cutting direction and depth. In the surgery, the surgeon searches the patient's lesion with the naked eye or by aid of a microscope. If the patient's lesion is deeply embedded in the normal brain tissues, the surgeon has to search the patient's lesion and cut the normal tissue simultaneously.

For solving the above-mentioned problems, the Brain LAB introduced a Vector-Vision surgical navigation system which includes a computer host movable on the floor and provided with castors, a monitor mounted on the computer host, two robot arms, two digital video cameras mounted on the robot arms respectively, a surgical instrument, and a positioning device (such as at least one positioning ball) mounted on the surgical instrument.

When in use, the two-dimensional cross-sectional images of the computed tomography or nuclear magnetic resonance of the patient are loaded into the computer host before surgery. Then, the computer host rebuilds and calculates the input data to obtain a three-dimensional image which is shown in the monitor, wherein the position of the patient's lesion and many characteristic coordinates are labeled in the three-dimensional image to function as the basis of the practical alignment of the patient during operation and the lesion positioning standard location.

The positioning device includes a plurality of fluorescent components which represent the point coordinates of the target (the surgical instrument). The digital video cameras simulate the spatial vision of the two eyes, monitor and capture the images of the fluorescent components, and transmit the captured image information to the computer host which calculates and obtains the relative distance, direction and angle between the surgical instrument and the patient's lesion, and further obtains the coordinate locations of the surgical instrument in the operation space. Thus, when the surgical instrument approaches the patient's lesion or when the direction and angle are under a wrong condition, the computer host will emit an alarm signal through the monitor (which emits a message) or an external sounder (which emits a warning sound).

The digital video cameras successively detect the positioning device during the surgery. The computer host calculates and derives the instantaneous coordinates, direction and angle of the surgical instrument. In addition, the computer host stores the previously obtained relative information of the surgical instrument. Thus, a picture simulating operation of the surgical instrument is added in the spatial image to provide a reference to the surgeon so as to facilitate the surgeon proceeding the surgical operation.

BRIEF SUMMARY OF THE INVENTION

The primary objective of the present invention is to provide an object guide system with interactive and programmable guiding functions.

In accordance with the present invention, there is provided, an object guide system comprising a plurality of light projecting devices, at least one image capture device, a control device electrically coupled with the light projecting devices, and a display unit electrically coupled with the at least one image capture device and the control device. Each of the light projecting devices emits and projects a light beam outward to an operation space. The light beams of the light projecting devices intersect and form an intersection light point in the operation space. The at least one image capture device captures the intersection light point projected into the operation space. The control device includes an input unit and a calculation unit. The input unit of the control device inputs three-dimensional data from the light projecting devices and delivers the three-dimensional data into the calculation unit. The calculation unit of the control device calculates the three-dimensional data from the input unit. The display unit receives the three-dimensional data transmitted by the control device or receives an information of the intersection light point transmitted and captured by the at least one image capture device.

Preferably, the object guide system further comprises an object on which the intersection light point is projected and indicated.

Preferably, the at least one image capture device captures the image cross information of the intersection light point in the operation space and the three-dimensional position information of the object. The calculation unit of the control device calculates the information to obtain the position of the object in the operation space.

Preferably, the at least one image capture device captures the intersection light point and proceeds interactive and guiding operations.

Preferably, the intersection light point formed by the light beams of the light projecting devices is a face or an image.

According to the primary advantage of the present invention, the object guide system uses the images of the intersection light point to proceed an interactive and programmable guiding operation in the operation space.

Further benefits and advantages of the present invention will become apparent after a careful reading of the detailed description with appropriate reference to the accompanying drawings.

BRIEF DESCRIPTION OF THE SEVERAL VIEWS OF THE DRAWING(S)

DETAILED DESCRIPTION OF THE INVENTION

Figure 1:
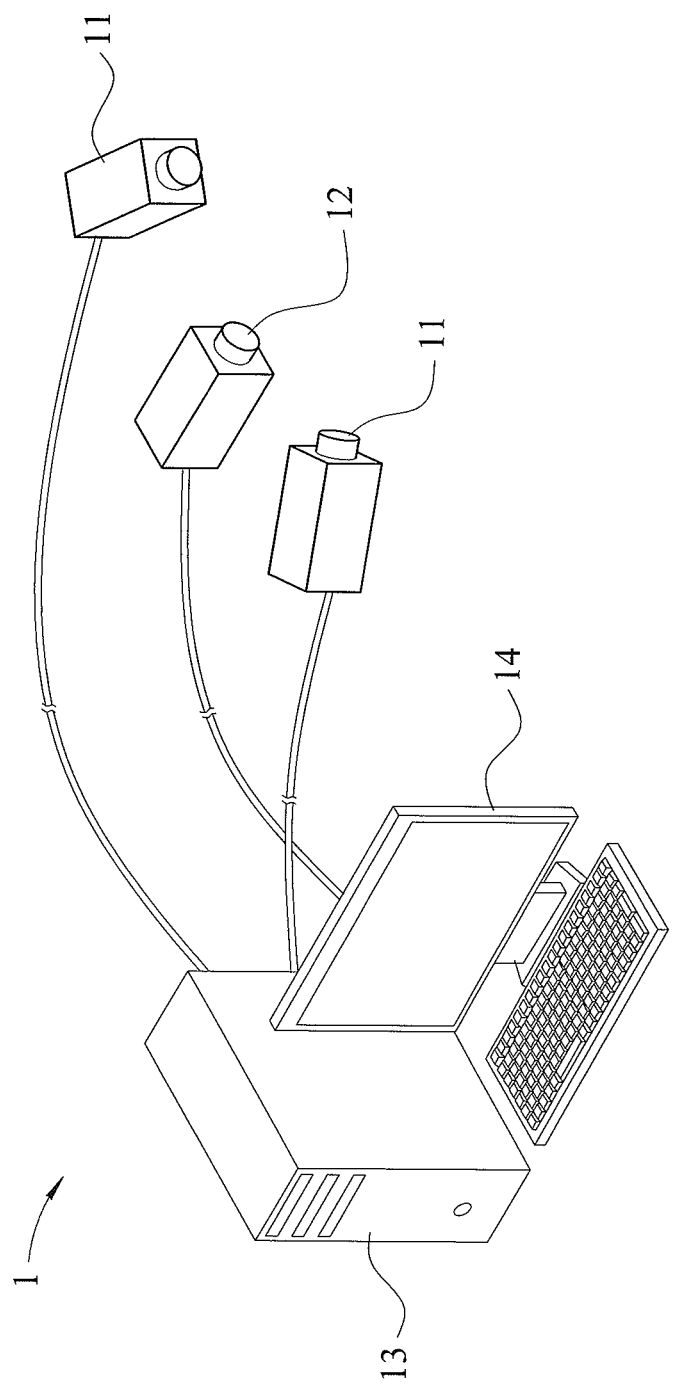
FIG. 1 is a perspective view of an object guide system in accordance with the preferred embodiment of the present invention.
Figure 2:
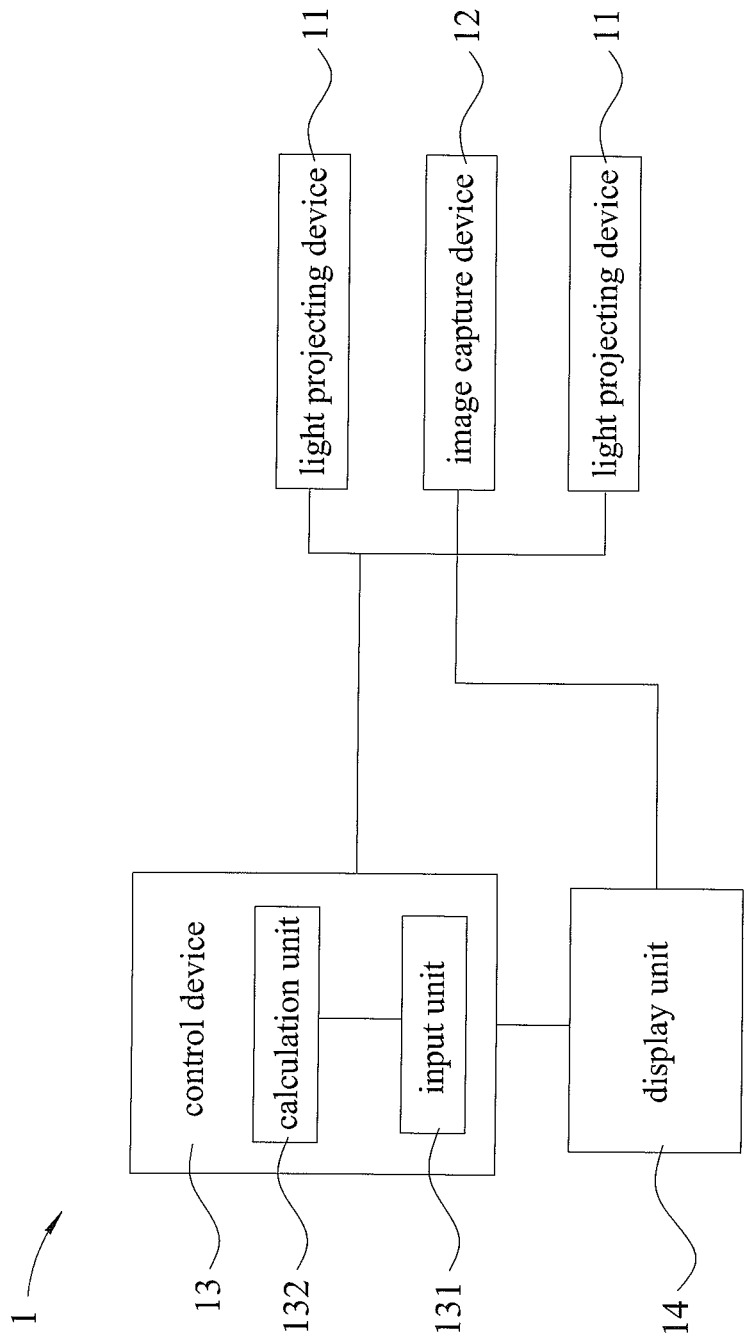
FIG. 2 is a block diagram view of the object guide system as shown in FIG. 1.
Figure 3:
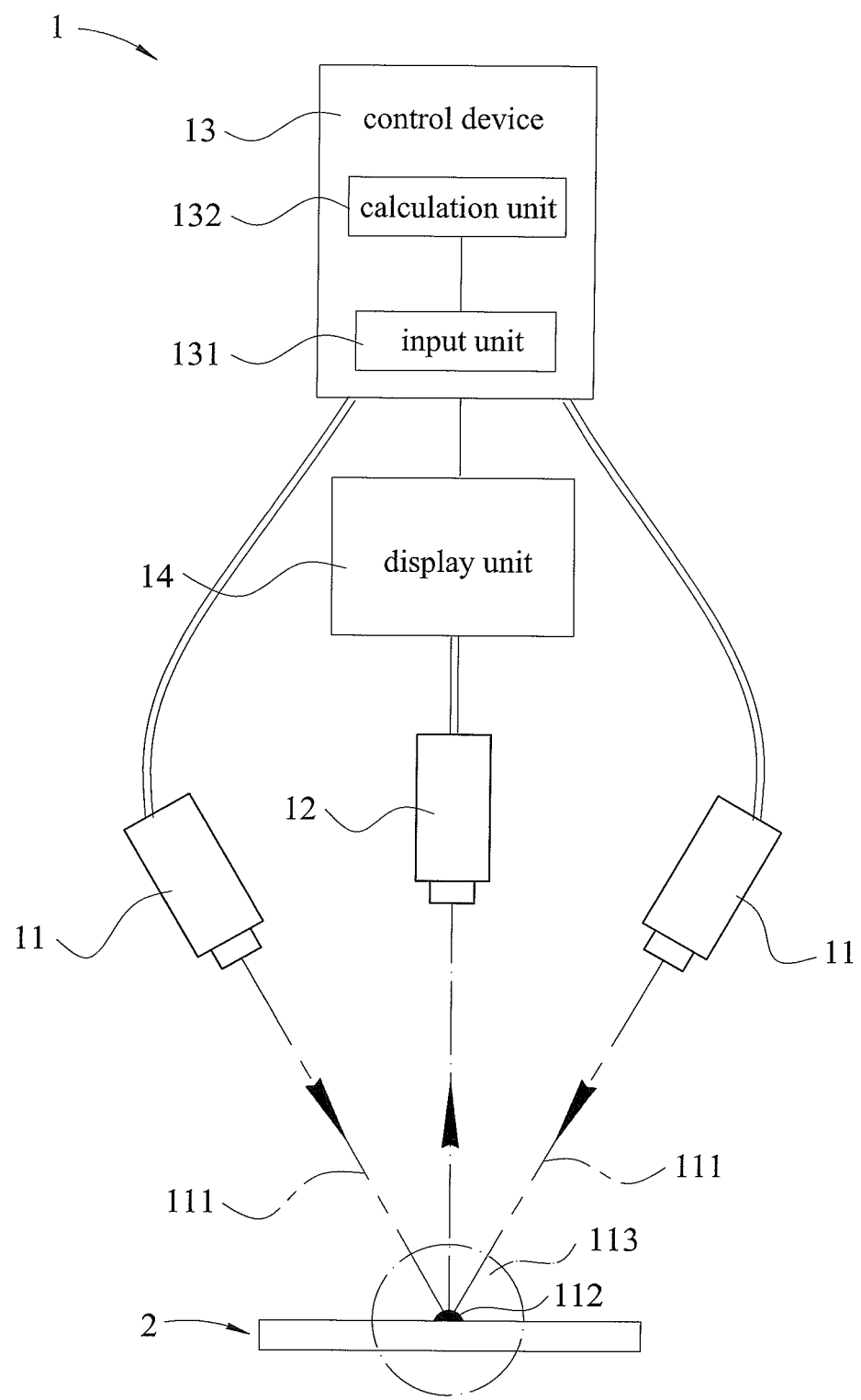
FIG. 3 is a schematic operational block diagram of the object guide system as shown in FIG. 1.
Figure 4:
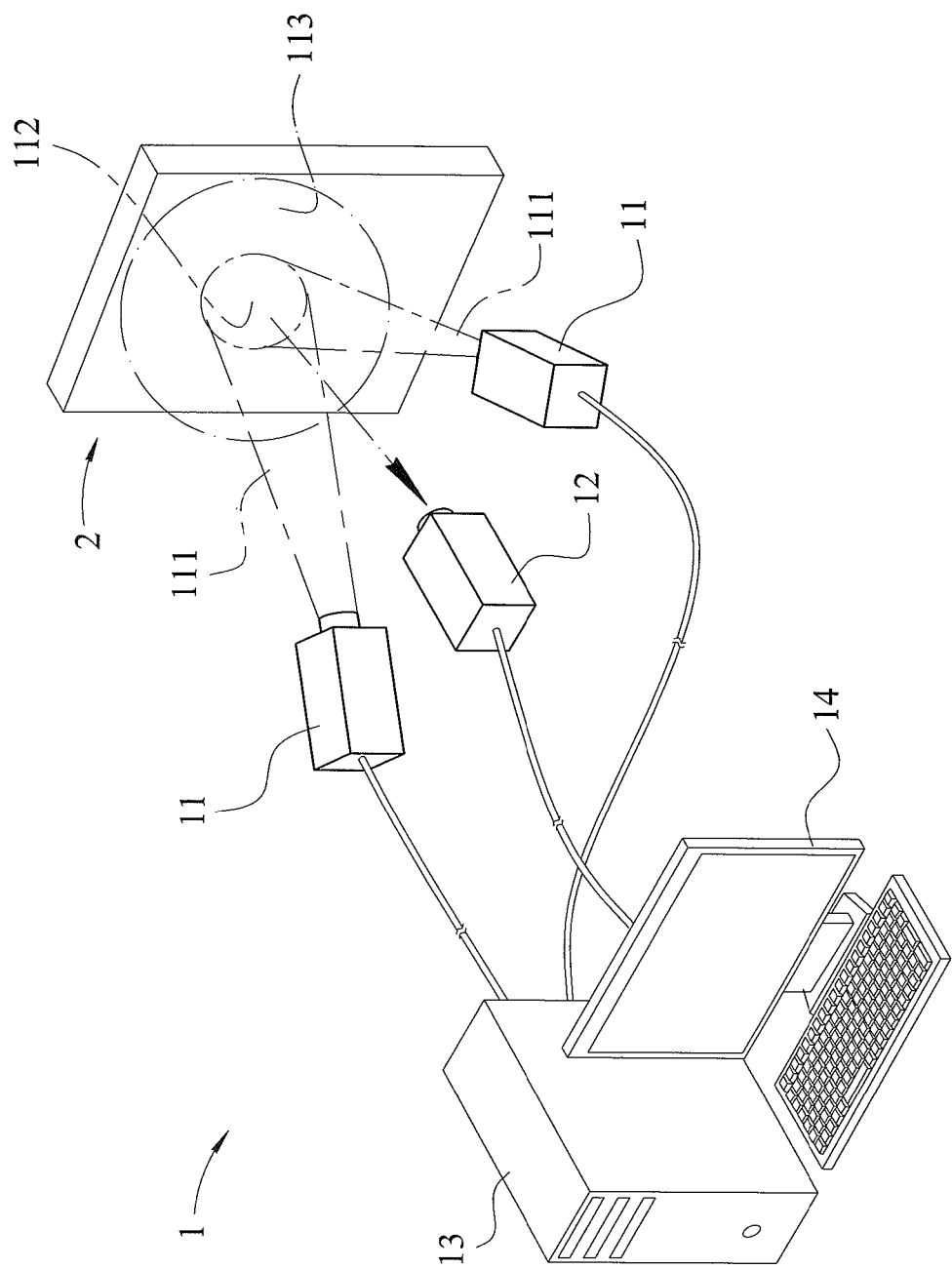
FIG. 4 is a schematic operational view of the object guide system as shown in FIG. 1.

Referring to the drawings and initially to FIGS. 1-4, an object guide system 1 in accordance with the preferred embodiment of the present invention comprises a plurality of light projecting devices 11, at least one image capture device 12, a control device 13 electrically coupled with the light projecting devices 11, and a display unit 14 electrically coupled with the at least one image capture device 12 and the control device 13.

Each of the light projecting devices 11 is preferably a projector, a laser, an optical projector or any other instrument that is capable of projecting visible or invisible rays onto a space. Each of the light projecting devices 11 emits and projects a light beam 111 outward to an operation space 113 through one or more different orientations. The light beams 111 of the light projecting devices 11 intersect and form an intersection light point 112 in the operation space 113. Preferably, the intersection light point 112 formed by the light beams 111 of the light projecting devices 11 is a face or an image.

The at least one image capture device 12 is preferably a camera, a video camera, an infrared video camera or any other instrument that can capture a natural light frequency. The at least one image capture device 12 captures the intersection light point 112 projected into the operation space 113.

The control device 13 includes an input unit 131 and a calculation unit 132. The input unit 131 of the control device 13 inputs three-dimensional data from the light projecting devices 11 and delivers the three-dimensional data into the calculation unit 132. The three-dimensional data from the light projecting devices 11 include the position and distance of an intersection point (such as the intersection light point 112) to be projected by the light projecting devices 11 before use. The calculation unit 132 of the control device 13 calculates the three-dimensional data from the input unit 131.

The display unit 14 receives the three-dimensional data transmitted by the control device 13 or receives an information of the intersection light point 112 transmitted and captured by the at least one image capture device 12.

The object guide system 1 further comprises an object 2 on which the intersection light point 112 is projected and indicated.

In practice, when the intersection light point 112 is formed in the operation space 113, the at least one image capture device 12 captures the image cross information of the intersection light point 112 in the operation space 113 and the three-dimensional position information of the object 2. Then, the three-dimensional data is transmitted from the at least one image capture device 12 to the input unit 131 of the control device 13. Then, the input unit 131 of the control device 13 delivers the three-dimensional data into the calculation unit 132. Then, the calculation unit 132 of the control device 13 calculates the three-dimensional data from the input unit 131 to obtain the position of the object 2 in the operation space 113. Then, the display unit 14 indicates the image information of the intersection light point 112 that is formed on the object 2 which is captured by the at least one image capture device 12 to proceed interactive and guiding functions. In such a manner, the object guide system 1 uses the images of the intersection light point 112 to proceed an interactive and programmable guiding operation.

Figure 5:
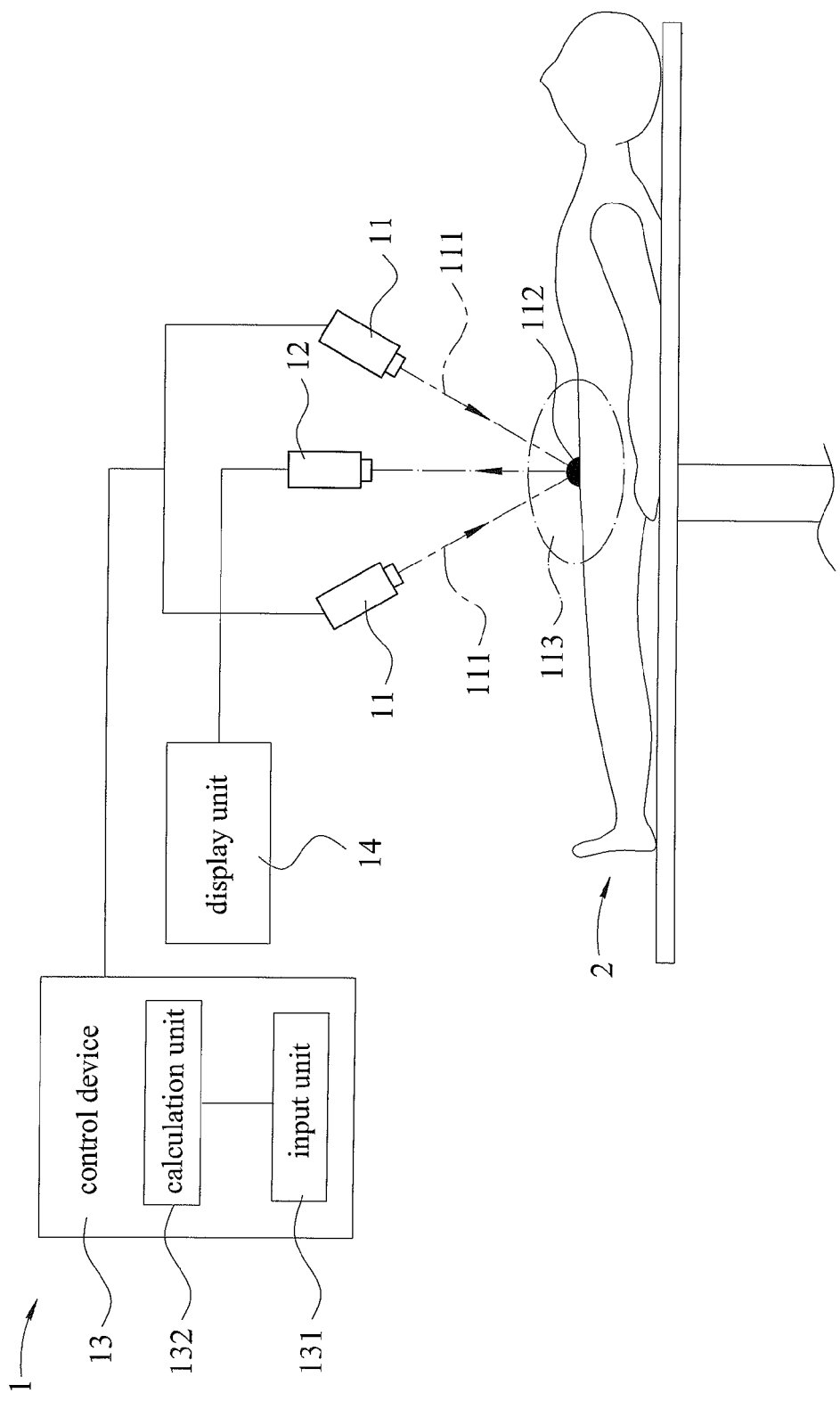
FIG. 5 is a schematic operational view of the object guide system as shown in FIG. 1 in use.

In operation, referring to FIG. 5 with reference to FIGS. 1-4, when the object guide system 1 in accordance with the preferred embodiment of the present invention is operated for a medical use, the object 2 is a patient. The three-dimensional data of the position and distance of the place to be projected are initially calculated. Then, each of the light projecting devices 11 emits the light beam 111 outward to an operation space 113 through one or more different orientations, and the light beams 111 of the light projecting devices 11 intersect and form the intersection light point 112 in the operation space 113. At this time, the intersection light point 112 is indicated on the object 2. Then, the at least one image capture device 12 captures the cross information of the operation space 113 and the three-dimensional position information of the object 2. Then, the calculation unit 132 of the control device 13 calculates and obtains the characteristic coordinates of the object 2 (that may being moving) in the operation space 113 to function as the basis of the practical alignment of the patient during operation and the lesion positioning standard location. Then, the control device 13 transmits the information to the display unit 14, so that the display unit 14 indicates the image information to proceed an interactive and guiding operation. It is to be noted that, the calculation unit 132 of the control device 13 calculates and program or change the characteristic coordinates of the object 2.

Thus, the at least one image capture device 12 can capture the cross information of the operation space 113 and the three-dimensional position information images of the object 2. In such a manner, the operating directions and positions of the surgical tools and instruments that are necessary for the surgeon during the interactive and guiding surgery operation can be determined by the object guide system 1. Alternatively, the programmed information before the surgery indicates the operating directions and positions of the surgical tools and instruments during the interactive and guiding surgery operation. Thus, when the object 2 is moving, the cross information of the operation space 113 and the three-dimensional position information images of the object 2 captured by the at least one image capture device 12 are changed and updated simultaneously, without having to additionally mount a positioning device (such as a positioning ball) on the surgical tools and instruments, so as to solve the tracking or guiding requirement of the surgical instruments of the conventional navigation tracking system.

In another preferred embodiment of the present invention, the object guide system 1 is available for an amusement use (such as a video game) or a manufacturing industry. When in use, the display unit 14 instantaneously indicates the guiding messages or interactive space position in the operation space 113 by co-operation of the light projecting devices 11 and the at least one image capture device 12. In such a manner, when the object 2 enters the operation space 113, the projected information is imaged on the object 2. Then, the at least one image capture device 12 captures the cross information of the operation space 113 and the three-dimensional position information of the object 2. Then, the calculation unit 132 of the control device 13 calculates and obtains the characteristic coordinates of the object 2 that is moving in the operation space 113. Thus, after the at least one image capture device 12 captures the cross information of the operation space 113 and the three-dimensional position information of the object 2, the object guide system 1 proceeds interactive and guiding operations.

Accordingly, the object guide system 1 uses the images of the intersection light point 112 to proceed an interactive and programmable guiding operation in the operation space 113.

Although the invention has been explained in relation to its preferred embodiment(s) as mentioned above, it is to be understood that many other possible modifications and variations can be made without departing from the scope of the present invention. It is, therefore, contemplated that the appended claim or claims will cover such modifications and variations that fall within the true scope of the invention.

The invention claimed is:

1. An object guide system comprising:
a plurality of light projecting devices;
at least one image capture device;
a control device electrically coupled with the light projecting devices;

and a display unit electrically coupled with the at least one image capture device and the control device; wherein:

the light projecting devices emit and project light beams from a same position or different positions to an operation space;

the light beams of the light projecting devices intersect and form at least one intersection light point in the operation space;

the at least one image capture device captures the at least one intersection light point projected into the operation space;

the control device includes an input unit and a calculation unit;

the input unit of the control device inputs three-dimensional data which comprising a position and a distance of the at least one intersection point and delivers the three-dimensional data into the calculation unit, wherein the three-dimensional data is pre-formed before the light projecting devices project the light beams;

the calculation unit of the control device calculates the three-dimensional data from the input unit;

the display unit receives the three-dimensional data transmitted by the control device or receives an information of the intersection light point transmitted and captured by the at least one image capture device; and wherein the at least one intersection light point is located in the air and is originally invisible, when an object is entered into the operation space and is located on the intersection light point, the intersection light point becomes visible, and the object located on the intersection light point is projected and indicated, thereby operations of the object is interacted and guided by the intersection light point.

2. The object guide system of claim 1, wherein:

the at least one image capture device captures the image cross information of the intersection light point in the operation space and the three-dimensional position information of the object; and the calculation unit of the control device calculates the information to obtain the position of the object in the operation space.

3. The object guide system of claim 1, wherein the intersection light point formed by the light beams of the light projecting devices is a face or an image.

* * * * *